(12) United States Patent
Clark et al.

(10) Patent No.: US 7,849,751 B2
(45) Date of Patent: Dec. 14, 2010

(54) CONTACT SENSORS AND METHODS FOR MAKING SAME

(75) Inventors: Andrew C. Clark, Clemson, SC (US); Martine LaBerge, Seneca, SC (US)

(73) Assignee: Clemson University Research Foundation, Clemson, SC (US)

( * ) Notice: Subject to any disclaimer, the term of this patent is extended or adjusted under 35 U.S.C. 154(b) by 1704 days.

(21) Appl. No.: 11/058,433

(22) Filed: Feb. 15, 2005

(65) Prior Publication Data

US 2006/0184067 A1    Aug. 17, 2006

(51) Int. Cl.
*G01L 1/00*    (2006.01)
*A61F 2/38*    (2006.01)

(52) U.S. Cl. .................... 73/768; 73/862.68; 623/20.14
(58) Field of Classification Search .................. 73/777, 73/768, 775, 862.68; 623/20.14–20.36, 18.11; 600/587
See application file for complete search history.

(56) References Cited

U.S. PATENT DOCUMENTS

| | | | |
|---|---|---|---|
| 4,145,317 A | | 3/1979 | Sado et al. |
| 4,273,682 A | | 6/1981 | Kanamori |
| 4,302,361 A | | 11/1981 | Kotani et al. |
| 4,314,227 A | | 2/1982 | Eventoff |
| 4,394,773 A | * | 7/1983 | Ruell .......................... 382/124 |
| 4,489,302 A | | 12/1984 | Eventoff |
| 4,492,949 A | * | 1/1985 | Peterson et al. ........ 73/862.046 |
| 4,495,236 A | | 1/1985 | Obara et al. |
| 4,553,837 A | * | 11/1985 | Marcus .......................... 356/71 |
| 4,634,623 A | | 1/1987 | Watkins |
| 4,734,034 A | * | 3/1988 | Maness et al. .............. 73/865.7 |
| 4,856,993 A | | 8/1989 | Maness et al. |
| 5,033,291 A | | 7/1991 | Podoloff et al. |
| 5,042,504 A | | 8/1991 | Huberti |
| 5,083,573 A | | 1/1992 | Arms |
| 5,197,488 A | | 3/1993 | Kovacevic |
| 5,302,936 A | | 4/1994 | Yaniger |
| 5,360,016 A | | 11/1994 | Kovacevic |
| 5,422,061 A | | 6/1995 | Takahashi et al. |
| 5,470,354 A | | 11/1995 | Hershberger et al. |

(Continued)

OTHER PUBLICATIONS

Clark, Andrew. Summer Internship. Available online Sep. 21, 2003. Accessed Jan. 26, 2010 <http://web.archive.org/web/20030921125459/http://www.clemson.edu/agbioeng/bio/andrew.htm>.*

(Continued)

*Primary Examiner*—Lisa M Caputo
*Assistant Examiner*—Jonathan Dunlap
(74) *Attorney, Agent, or Firm*—Ballard Spahr LLP

(57) ABSTRACT

The present invention is directed to novel contact sensors. The contact sensors of the invention include a conductive composite material formed of a polymer and a conductive filler. In one particular embodiment, the composite materials can include less than about 10 wt % conductive filler. Thus, the composite material of the contact sensors can have physical characteristics essentially identical to the polymer, while being electrically conductive with the electrical resistance proportional to the load on the sensor. If desired, the sensors can be formed of the same polymeric material as the bearing that is being examined. The sensors can provide real time dynamic contact information for joint members under conditions expected during use. In one particular embodiment, the sensors can be used to examine dynamic wear characteristics of artificial joint bearings such as artificial knee, hip, or shoulder bearings.

23 Claims, 11 Drawing Sheets

U.S. PATENT DOCUMENTS

| | | | |
|---|---|---|---|
| 5,541,570 | A | 7/1996 | McDowell |
| 5,756,904 | A | 5/1998 | Oreper et al. |
| 5,818,956 | A * | 10/1998 | Tuli .......................... 382/126 |
| 5,880,976 | A | 3/1999 | DiGioia, III et al. |
| 5,989,700 | A | 11/1999 | Krivopal |
| 5,993,400 | A | 11/1999 | Rincoe et al. |
| 6,032,542 | A | 3/2000 | Warnick et al. |
| 6,136,412 | A | 10/2000 | Spiewak et al. |
| 6,207,775 | B1 | 3/2001 | Marti et al. |
| 6,216,545 | B1 | 4/2001 | Taylor |
| 6,267,011 | B1 | 7/2001 | Kurtz et al. |
| 6,273,863 | B1 | 8/2001 | Avni |
| 6,283,829 | B1 | 9/2001 | Molnar |
| 6,319,293 | B1 | 11/2001 | Debe et al. |
| 6,441,084 | B1 | 8/2002 | Lee et al. |
| 6,447,448 | B1 | 9/2002 | Ishikawa et al. |
| 6,524,742 | B1 | 2/2003 | Emanuel et al. |
| 6,543,299 | B2 | 4/2003 | Taylor |
| 6,583,630 | B2 | 6/2003 | Mendes et al. |
| 6,693,441 | B2 * | 2/2004 | Lane et al. .................. 324/662 |
| 6,769,313 | B2 | 8/2004 | Weiss |
| 6,877,385 | B2 | 4/2005 | Fang et al. |
| 7,080,562 | B2 * | 7/2006 | Knowles et al. ............... 73/818 |
| 7,097,662 | B2 * | 8/2006 | Evans, III et al. ........ 623/18.11 |
| 7,162,322 | B2 | 1/2007 | Arbogast |
| 7,182,736 | B2 | 2/2007 | Roy et al. |
| 7,258,026 | B2 | 8/2007 | Papakostas et al. |
| 7,311,009 | B2 | 12/2007 | Kotovsky |
| 7,377,944 | B2 | 5/2008 | Janusson et al. |
| 7,406,386 | B2 | 7/2008 | Brett et al. |
| 7,470,288 | B2 * | 12/2008 | Dietz et al. ............... 623/20.14 |
| 2003/0069644 | A1 * | 4/2003 | Kovacevic et al. ....... 623/18.11 |
| 2004/0019382 | A1 | 1/2004 | Amirouche et al. |
| 2004/0019384 | A1 * | 1/2004 | Kirking et al. ........... 623/18.11 |
| 2004/0064191 | A1 * | 4/2004 | Wasielewski ............ 623/20.14 |
| 2005/0010302 | A1 * | 1/2005 | Dietz et al. ............... 623/20.14 |
| 2005/0177170 | A1 | 8/2005 | Fisher et al. |
| 2005/0273170 | A1 * | 12/2005 | Navarro et al. ........... 623/17.13 |
| 2006/0047283 | A1 * | 3/2006 | Evans et al. .............. 623/18.11 |
| 2007/0234819 | A1 * | 10/2007 | Amirouche et al. ........... 73/781 |
| 2008/0065225 | A1 * | 3/2008 | Wasielewski et al. .... 623/18.11 |

OTHER PUBLICATIONS 958-203, DuPont Material Safety Data Sheet. Original 2003. Available Apr. 24, 2006 online. <http://www.customcoatingsinternational.com/958-203_051128_2_MSDS.pdf>.*

Abstract—*Measurement of Dynamic Contact Area and Lubrication Modes in a Highly Conforming and Standard Conforming Tibial Insert Using Polymeric Doping Technology*, A. C. Clark, J. D. DesJardins, T. B Pace, and M. LaBerge, Transactions of the 51$^{st}$ Annual Meeting of the Orthopaedic Research Society, vol. 30, 0568, Jan. 2005, 1 page.

Article—*Analysis of the effect of pressure on compression moulding of UHMWPE*, N. C. Parasnis and K. Ramani, Journal of Materials Science: Materials in Medicine, vol. 9, 1998, pp. 165-172.

Article—*Ultra-High Molecular Weight Polyethylene*, Stephen Li and Albert H. Burstein, The Journal of Bone and Joint Surgery, vol. 76-A, No. 7, Jul. 1994, pp. 1080-1090.

Andrew Clark, "Summer Internship in the Department of Bioengineering at Clemson University", Poster displayed Apr. 2001.

* cited by examiner

CONTACT SENSORS AND METHODS FOR MAKING SAME

BACKGROUND OF THE INVENTION

Contact sensors have been used to gather information concerning contact or near-contact between two surfaces in medical applications, such as dentistry, podiatry, and in the development of prostheses, as well as in industrial applications, for instance to determine load and uniformity of pressure between mating surfaces, and in the development of bearings and gaskets. In general, these sensors include pressure-sensitive films designed to be placed between mating surfaces. These film sensors, while generally suitable for examining static contact characteristics between two generally flat surfaces, have presented many difficulties in other situations. For instance, when examining contact data between more complex surfaces, surfaces including complex curvatures, for instance, it can be difficult to conform the films to fit the surfaces without degrading the sensor's performance.

More serious problems exist with these materials as well. For instance, film-based contact sensor devices and methods introduce a foreign material having some thickness between the mating surfaces, which can change the contact characteristic of the junction and overestimate the contact areas between the two surfaces. Moreover, the ability to examine real time, dynamic contact characteristics is practically non-existent with these types of sensors.

A better understanding of the contact conditions at joints and junctions could lead to reduced wear in materials, better fit between mating surfaces, and longer life expectancy for machined parts. For example, one of the leading causes of failure in total joint replacement prostheses is due to loosening of the implant induced by wear debris particles worn from the polymeric bearing component. A better understanding of the contact conditions between the joint components would lead to reduced implant wear and longer implant life.

What is needed in the art are contact sensors that can provide more accurate and/or dynamic contact information concerning a junction formed between two surfaces of any surface shape.

SUMMARY OF THE INVENTION

In one embodiment, the present invention is directed to a contact sensor. The sensor includes an electrically conductive composite material comprising a polymer and a conductive filler. Generally, the composite material can include any polymer. In certain embodiments, the polymer can be an engineering polymer or a high performance polymer. In one preferred embodiment, the composite material can include ultra-high molecular weight polyethylene (UHMWPE). In one embodiment, the composite material of the sensors can include less than about 10 wt % of a conductive filler. For example, the composite material can comprise less than about 8 wt % of a conductive filler. In one embodiment, the composite material can comprise less that about 5 wt % of a conductive filler. The conductive filler can be any suitable material. For example, in one embodiment, the conductive filler can include carbon black.

The contact sensors of the invention can define an essentially inflexible contact surface. As such, a surface of the contact sensors of the invention can be formed so as to replicate, a surface that can be placed in proximity to a surface of a second member so as to form a junction. In particular, the contact surface of the sensors of the invention can replicate the shape and optionally also the material characteristics of a junction-forming member found in an industrial, medical, or any other useful setting. For example, in one particular embodiment, the essentially inflexible contact surface of the sensor can include curvature such as that described by the contact surface of a polymeric bearing portion of an implantable artificial replacement joint such as the polymeric bearing portion of a hip, knee, or shoulder replacement joint.

In one embodiment, the sensor can be formed entirely of the composite material. In another embodiment, the contact sensors of the invention can include one or more discrete regions of the electrically conductive composite material and a non-conductive material. For example, the sensors can include multiple discrete regions of the electrically conductive composite material that can be separated by an intervening nonconductive material, e.g., an intervening polymeric material. In one particular embodiment, the intervening polymeric material separating discrete regions of the composite material can include the same polymer as the polymer of the electrically conductive composite material.

In one embodiment, the electrically conductive composite material can be located at the contact surface of the sensor for obtaining surface contact data. If desired, the sensor can include composite material that can be confined within the sensor, at a depth below the contact surface, in order to obtain internal stress data.

The electrically conductive composite material of the present invention can, in one particular embodiment, be formed by mixing a polymer in particulate form with a conductive filler in particulate form. According to this embodiment, in order to completely coat the polymer granules with the granules of the conductive filler, the granule size of the polymer can be at least about two orders of magnitude larger than the granule size of the conductive filler. For instance, the average granule size of the polymer can, in one embodiment, be between about 50 µm and about 500 µm. The average granule size of the conductive filler can be, for example, between about 10 nm and about 500 nm.

Following a mixing step, the composite conductive material can be formed into the sensor shape either with or without areas of non-conductive material in the sensor, as desired, by, for example, compression molding, RAM extrusion, or injection molding. If desired, a curvature can be formed into the contact surface of the sensor in the molding step or optionally in a secondary forming step such as a machining or cutting step.

During use, the sensors of the invention can be located in association with a member so as to form a contact junction between a surface of the member and the contact surface of the sensor. The sensor can then be placed in electrical communication with a data acquisition terminal, for instance via a fixed or unfixed hard-wired or a wireless communication circuit, and data can be gathered concerning contact between the sensor and the member. In one particular embodiment, dynamic contact data can be gathered. For instance, any or all of contact stress data, internal stress data, load, impact data, lubrication regime data, and/or information concerning wear, such as wear mode information can be gathered.

In another embodiment, the disclosed sensors can be integrated with the part that they have been designed to replicate and actually used in the joint in the desired working setting. For example, the contact sensor can gather data while functioning as a bearing of a joint or junction in real time in an industrial, medical, or other working setting.

BRIEF DESCRIPTION OF THE FIGURES

A full and enabling disclosure of the present invention, including the best mode thereof, directed to one of ordinary skill in the art, is set forth more particularly in the remainder of the specification, which makes reference to the appended figures in which.

Figure 1:
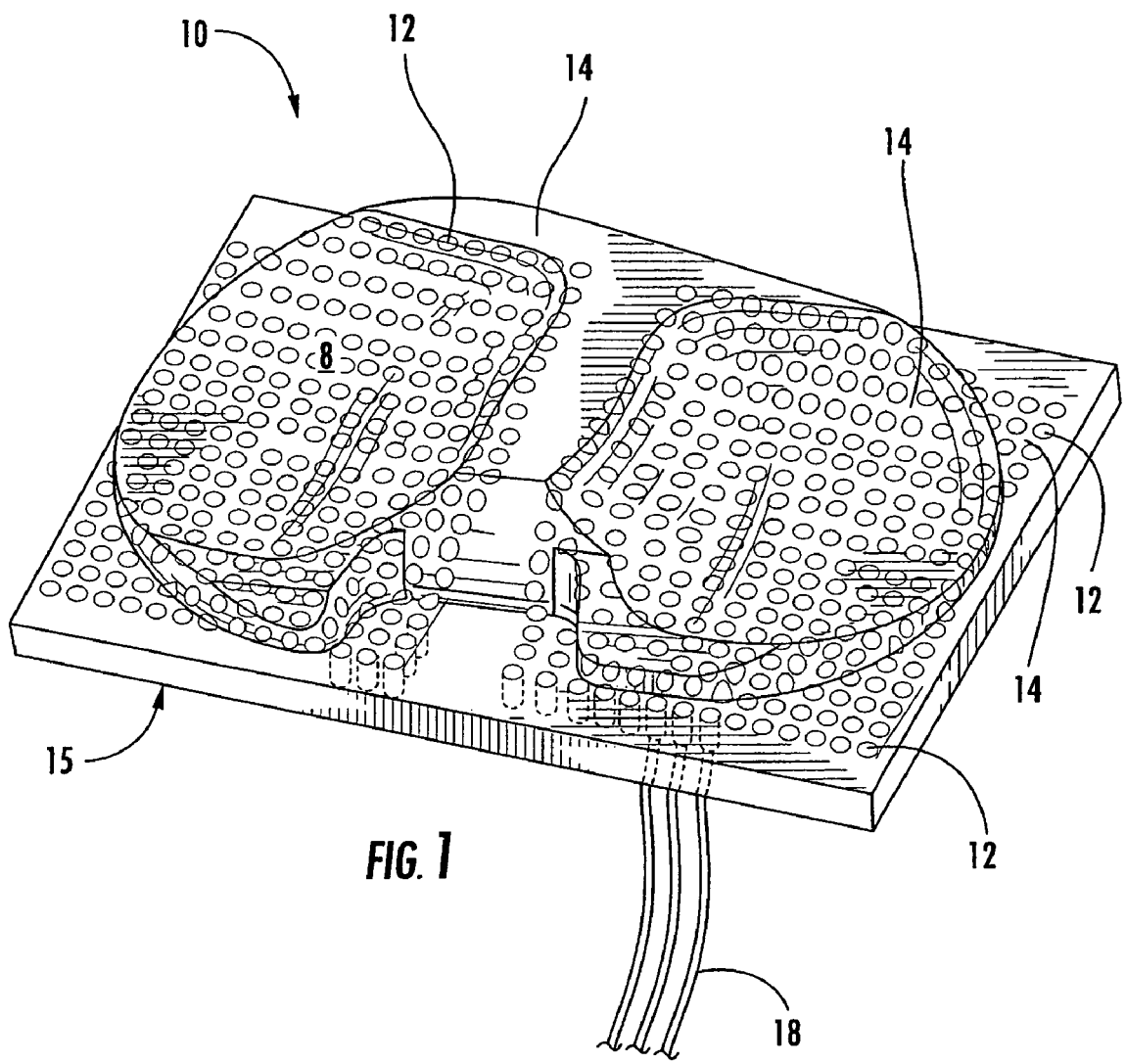
FIG. 1 illustrates one embodiment of the present invention for obtaining surface contact data of a junction.

Repeat use of references characters in the present specification and drawings is intended to represent same or analogous features or elements of the invention.

DEFINITION OF TERMS

For purposes of the present disclosure, the following terms are herein defined as follows:

The term primary particle is intended to refer to the smallest particle, generally spheroid, of a material such as carbon black.

The term aggregate is intended to refer to the smallest unit of a material, and in particular, of carbon black, found in a dispersion. Aggregates of carbon black are generally considered indivisible and are made up of multiple primary particles held together by strong attractive or physical forces.

The term granule is also intended to refer to the smallest unit of a material found in a dispersion. However, while a granule can also be an aggregate, such as when considering carbon black, this is not a requirement of the term. For example, a single granule of a polymer, such as UHMWPE or conventional grade polyethylene, for example can be a single unit.

The term agglomeration is intended to refer to a configuration of a material including multiple aggregates or granules loosely held together, as with Van der Waals forces. Agglomerations of material in a dispersion can often be broken down into smaller aggregates or granules upon application of sufficient energy so as to overcome the attractive forces.

The term 'conventional polymer' is intended to refer to polymers that have a thermal resistance below about 100° C. and relatively low physical properties. Examples include high-density polyethylene (PE), polystyrene (PS), polyvinyl chloride (PVC), and polypropylene (PP).

The term 'engineering polymer' is intended to refer to polymers that have a thermal resistance between about 100° C. and about 150° C. and exhibit higher physical properties, such as strength and wear resistance, as compared to conventional polymers. Examples include polycarbonates (PC), polyamides (PA), polyethylene terephthalate (PET), and ultrahigh molecular weight polyethylene (UHMWPE).

The term 'high performance polymer' is intended to refer to polymers that have a thermal resistance greater than about 150° C. and relatively high physical properties. Examples include polyetherether ketone (PEEK), polyether sulfone (PES), polyimides (PI), and liquid crystal polymers (LC).

Contact stress, synonymous with contact pressure, is herein defined as surface stress resulting from the mechanical interaction of two members. It is equivalent to the applied load (total force applied) divided by the area of contact.

Internal stress refers to the forces acting on an infinitely small unit area at any point within a material. Internal stress varies throughout a material and is dependent upon the geometry of the member as well as loading conditions and material properties.

Impact force is herein defined to refer to the time-dependent force one object exerts onto another object during a dynamic collision.

DETAILED DESCRIPTION OF THE INVENTION

It is to be understood by one of ordinary skill in the art that the present discussion is a description of exemplary embodiments only, and is not intended as limiting the broader aspects of the present invention which broader aspects are embodied in the exemplary construction.

The present invention is generally directed to contact sensors, methods of forming contact sensors, and methods of advantageously utilizing the sensors. In general, contact sensors can be utilized to gather dynamic and/or static contact data at the junction of two opposing members such as a junction found in a joint, a bearing, a coupling, a connection, or any other junction involving the mechanical interaction of two opposing members, and including junctions with either high or low tolerance values as well as junctions including intervening materials between the members, such as lubricated junctions, for instance. Dynamic and/or static data that can be gathered utilizing the disclosed sensors can include, for example, load data, lubrication regimes, wear modes, contact stress data, internal stress data, and/or impact data for a member forming the junction. The contact sensors of the present invention can provide extremely accurate data for the junction being examined, particularly in those embodiments wherein at least one of the members forming the junction in the working setting (as opposed, for instance, to a testing setting) is formed of a polymeric material.

Beneficially, the sensors of the present invention can include an essentially non-flexible surface that can be shaped to replicate either one of the mating surfaces forming the junction. As such, in a laboratory-type testing application, the sensor can simulate one member forming the junction, and contact data can be gathered for the junction under conditions closer to those expected during actual use, i.e., without altering the expected contact dynamics experienced at the junction during actual use. For instance, the disclosed sensors can provide contact data for the junction without the necessity of including extraneous testing material, such as dyes, thin films, or the like, within the junction itself.

In one embodiment, the sensor can be formed of a material that essentially duplicates the physical characteristics of the junction member that the sensor is replicating. Accordingly, in this embodiment, the sensor can exhibit wear characteristics essentially equivalent to those of the member when utilized in the field, providing even more accurate testing data. According to one particular embodiment of the invention, rather than being limited to merely simulating a junction-forming member, such as in a pure testing situation, the sensor can be incorporated into the member itself that is destined for use in the working application, i.e., in the field, and can provide contact data for the junction during actual use of the part, for instance in an industrial, medical, or other working setting.

The contact sensors of the present invention include an electrically conductive composite material that in turn includes at least one non-conductive polymer material combined with an electrically conductive filler. In one preferred embodiment, the composite material of the present invention can include an electrically conductive filler that can provide pressure sensitive electrical conductivity to the composite material, but can do so while maintaining the physical characteristics, e.g., wear resistance, hardness, etc., of the non-conductive polymeric material of the composite. Thus, in this embodiment, the sensors of the present invention can be developed to include a particular polymer or combination of polymers so as to essentially replicate the physical characteristics of the similar but non-conductive polymeric member forming the junction to be examined.

This combination of beneficial characteristics in the composite materials has been attained through recognition and/or development of processes for forming the composite materials in which only a small amount of the electrically conductive filler need be combined with the polymeric material. As such, the physical characteristics of the composite material can more closely resemble those of the starting polymeric material, and the sensor can closely replicate the physical characteristics of a non-conductive polymeric member forming a junction.

This feature can be particularly beneficial when considering the examination of junctions including at least one member formed of engineering and/or high performance polymers. When considering such materials, the addition of even a relatively small amount of additive or filler can drastically alter the physical characteristics that provide the desired performance of the materials. In the past, when attempts were made to form electrically conductive composites of many engineering and high performance polymers, the high levels of additives (greater than about 20% by weight, in most instances) that were required usually altered the physical characteristics of the polymeric material to the point that the conductive composite material formed no longer exhibited the desired characteristics of the starting, non-conductive material. Thus, the examination of junctions formed with such materials has in the past generally required the addition of an intervening material, such as a pressure sensitive film within the junction, leading to the problems discussed above.

It should be noted, however, that while the presently disclosed sensors can be of great benefit when formed to include engineering and/or high performance polymeric composite materials, this is not a requirement of the invention. In other embodiments, the polymer utilized to form the composite material can be a more conventional polymer. No matter what polymer, copolymer, or combination of polymers is used to form the disclosed composite conductive materials, the composite materials of the disclosed sensors can exhibit pressure sensitive electrical conductivity and if desired, can also be formed so as to essentially maintain the physical characteristics of a polymeric material identical to the composite but for the lack of the conductive filler.

In general, any polymeric material that can be combined with an electrically conductive filler to form a pressure sensitive conductive polymeric composite material that can then be formed into an essentially inflexible shape can be utilized in the present invention. For instance, various polyolefins, polyurethanes, polyester resins, epoxy resins, and the like can be utilized in the present invention. In certain embodiments, the composite material can include engineering and/or high performance polymeric materials. In one particular embodiment, the composite material can include UHMWPE. UHMWPE is generally classified as an engineering polymer, and possesses a unique combination of physical and mechanical properties that allows it to perform extremely well in rigorous wear conditions. In fact, it has the highest known impact strength of any thermoplastic presently made, and is highly resistant to abrasion, with a very low coefficient of friction. The physical characteristics of UHMWPE have made it attractive in a number of industrial and medical applications. For instance, it is commonly used in forming polymeric gears, sprockets, impact surfaces bearings, bushings and the like. In the medical industry, UHMWPE is commonly utilized in forming replacement joints including portions of artificial hips, knees, and shoulders. In addition, UHMWPE can be in particulate form at ambient conditions and can be shaped through compression molding or RAM extrusion and can optionally be machined to form an essentially inflexible block (i.e., not easily misshapen or distorted), with any desired surface shape.

Conductive fillers as are generally known in the art can be combined with the polymeric material of choice to form the composite material of the disclosed sensors. A non-limiting list of exemplary conductive fillers suitable for use in the present invention can include, for instance, carbon, gold, silver, aluminum, copper, chromium, nickel, platinum, tungsten, titanium, iron, zinc, lead, molybdenum, selenium, indium, bismuth, tin, magnesium, manganese, cobalt, titanium germanium, mercury, and the like.

According to one embodiment of the present invention, a pressure sensitive conductive composite material can be formed by combining a relatively small amount of a conductive filler with a polymeric material. For example, the composite can include less than about 10% by weight of the conductive filler. In one embodiment, the composite materials can include less than about 8% by weight of the conductive filler. In another embodiment, the composite material can include less than about 5% by weight filler, for instance, less than about 1 wt % in one embodiment. Of course, in other embodiments, such as those in which the physical characteristics of the composite material need not approach those of the non-conductive polymeric material, the composite material can include a higher weight percentage of the conductive filler material.

In general, the polymeric material and the conductive filler can be combined in any suitable fashion, which can generally be determined at least in part according to the characteristics of the polymeric material. For example, and depending upon the polymers involved, the materials can be combined by mixing at a temperature above the melting temperature of the polymer (conventional melt-mixing) and the filler materials can be added to the molten polymer, for instance, in a conventional screw extruder, paddle blender, ribbon blender, or any other conventional melt-mixing device. The materials can also be combined by mixing the materials in an appropriate solvent for the polymer (conventional solution-mixing or solvent-mixing) such that the polymer is in the aqueous state and the fillers can be added to the solution, optionally utilizing an appropriate surfactant if desired, following which the solvent can be allowed or encouraged to evaporate, resulting in the solid conductive composite material. In another embodiment, the materials can be mixed below the melting point of the polymer and in dry form, for instance, in a standard vortex mixer, a paddle blender, a ribbon blender, or the like, such that the dry materials are mixed together before further processing.

When mixing the components of the composite material, the mixing can be carried out at any suitable conditions. For instance, in one embodiment, the components of the composite material can be mixed at ambient conditions. In other embodiments, however, mixing conditions can be other than ambient, for instance so as to maintain the materials to be mixed in the desired physical state and/or to improve the mixing process.

When dry mixing the materials to be utilized in the composite, the exact particulate dimensions of the materials are not generally critical to the invention. However, in certain embodiments, the relative particulate size of the materials to be combined in the mixture can be important. In particular, the relative particulate size of the materials to be combined can be important in those embodiments wherein a relatively low amount of conductive filler is desired and in those embodiments wherein the polymer granules do not completely fluidize during processing. For instance, the relative particle size can be important in certain embodiments wherein engineering or high-performance polymers are utilized, and in particular, in those embodiments utilizing extremely high melt viscosity polymers such as UHMWPE, which can be converted via non-fluidizing conversion processes, such as compression molding or RAM extrusion processes.

In such embodiments, the particle size of the filler can beneficially be considerably smaller than the particle size of the polymer. According to this embodiment, and while not wishing to be bound by any particular theory, it is believed that due to the small size of the conductive filler particles relative to the larger polymer particles, the conductive filler is able to completely coat the polymer during mixing and, upon conversion of the composite polymeric powder in a non-fluidizing conversion process to the final solid form, the inter-particle distance of the conductive filler particles can remain above the percolation threshold such that the composite material can exhibit the desired electrical conductivity. According to this embodiment, when forming the composite mixture, the granule or aggregate size of the conductive filler to be mixed with the polymer can be at least about two orders of magnitude smaller than the granule size of the polymer. In some embodiments, the granule or aggregate size of the conductive filler can be at least about three orders of magnitude smaller than the granule size of the polymer.

Figure 5:
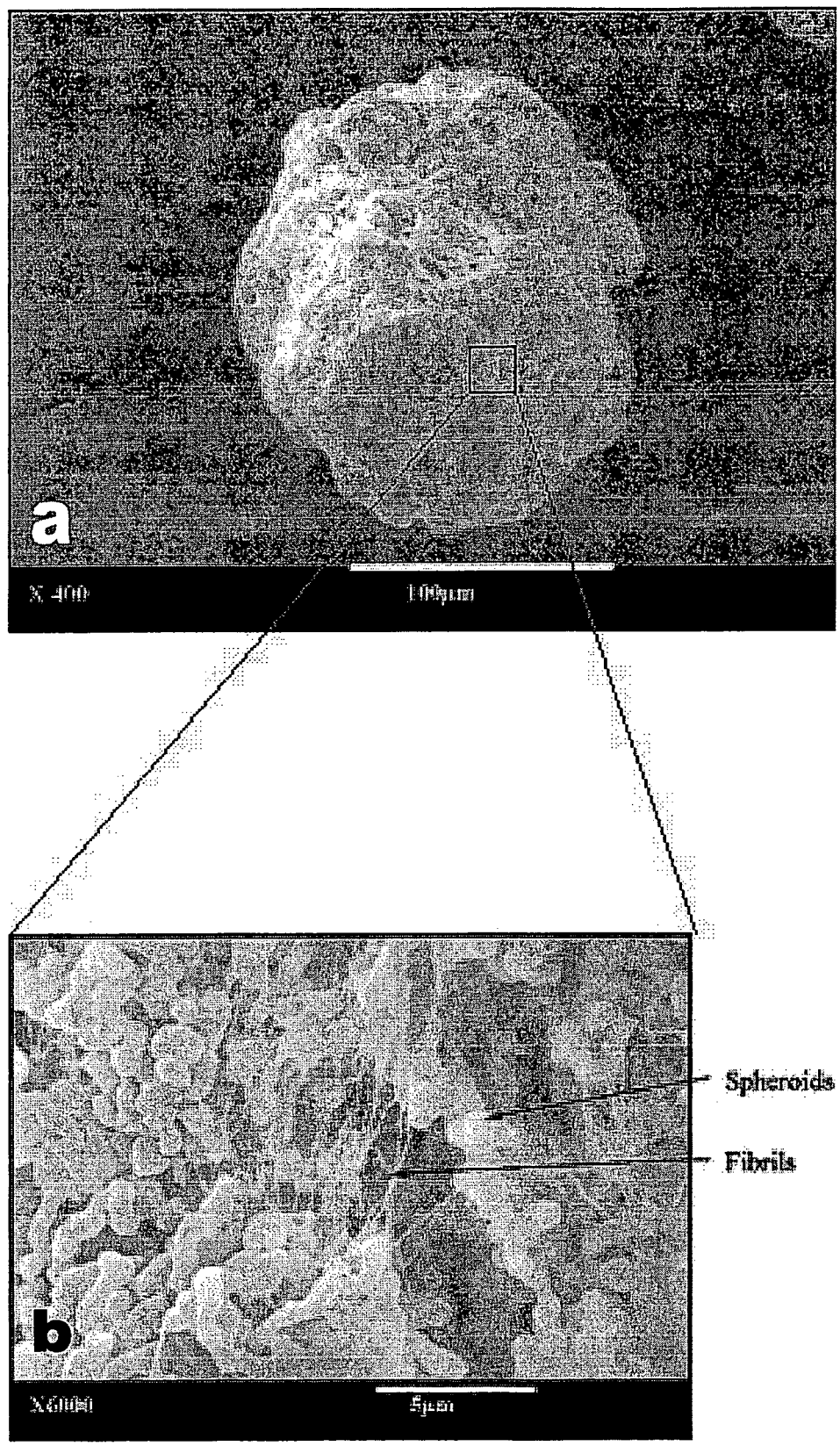
FIGS. 5A and 5B are SEM images of a single UHMWPE granule.

In forming the composite material of the present invention according to this embodiment, a granular polymer, such as the UHMWPE illustrated in FIG. 5, can be dry mixed with a conductive filler that is also in particulate form. FIG. 5A is an FESEM image of a single UHMWPE granule. The granule shown in FIG. 5A has a diameter of approximately 150 μm, though readily available UHMWPE in general can have a granule diameter in a range of from about 50 μm to about 200 μm. FIG. 5B is an enlarged FESEM image of the boxed area shown on FIG. 5A. As can be seen, the individual granule is made up of multiple sub-micron sized spheroids and nano-sized fibrils surrounded by varying amounts of free space.

Figure 4:
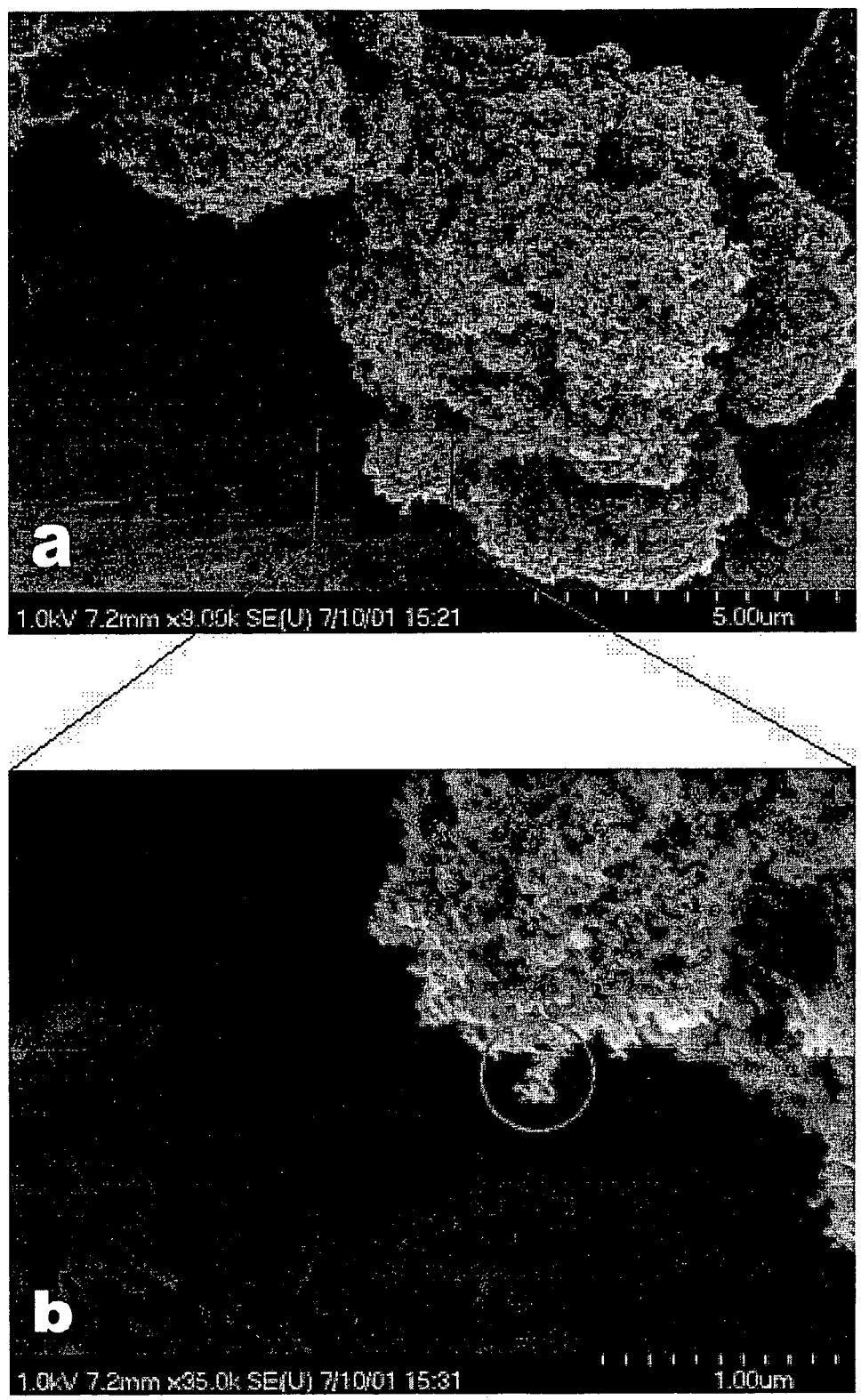
FIGS. 4A and 4B are SEM images of carbon black powder including images of primary particles, aggregates, and agglomerations.

In one embodiment, carbon black conductive filler can be mixed with the polymer. Carbon black is readily available in a wide variety of agglomerate sizes, generally ranging in diameter from about 1 μm to about 100 μm, that can be broken down into smaller aggregates of from about 10 nm to about 500 nm upon application of suitable energy. For example, FIG. 4A is an FESEM image of a carbon black powder agglomerate having a diameter of approximately 10 μm. In FIG. 4B, individual carbon black aggregates forming the agglomerate can clearly be distinguished. The circled section of FIG. 4B shows a single carbon black aggregate loosely attached to the larger agglomerate. As the scale of FIG. 4B illustrates, the aggregates in this particular image range in size from about 50 nm to about 500 nm. In the circled section of FIG. 4B can be seen the smaller, spherical primary particles of carbon black, the size of which are often utilized when classifying commercial carbon black preparations. These primary particles make up the aggregate.

Figure 6:
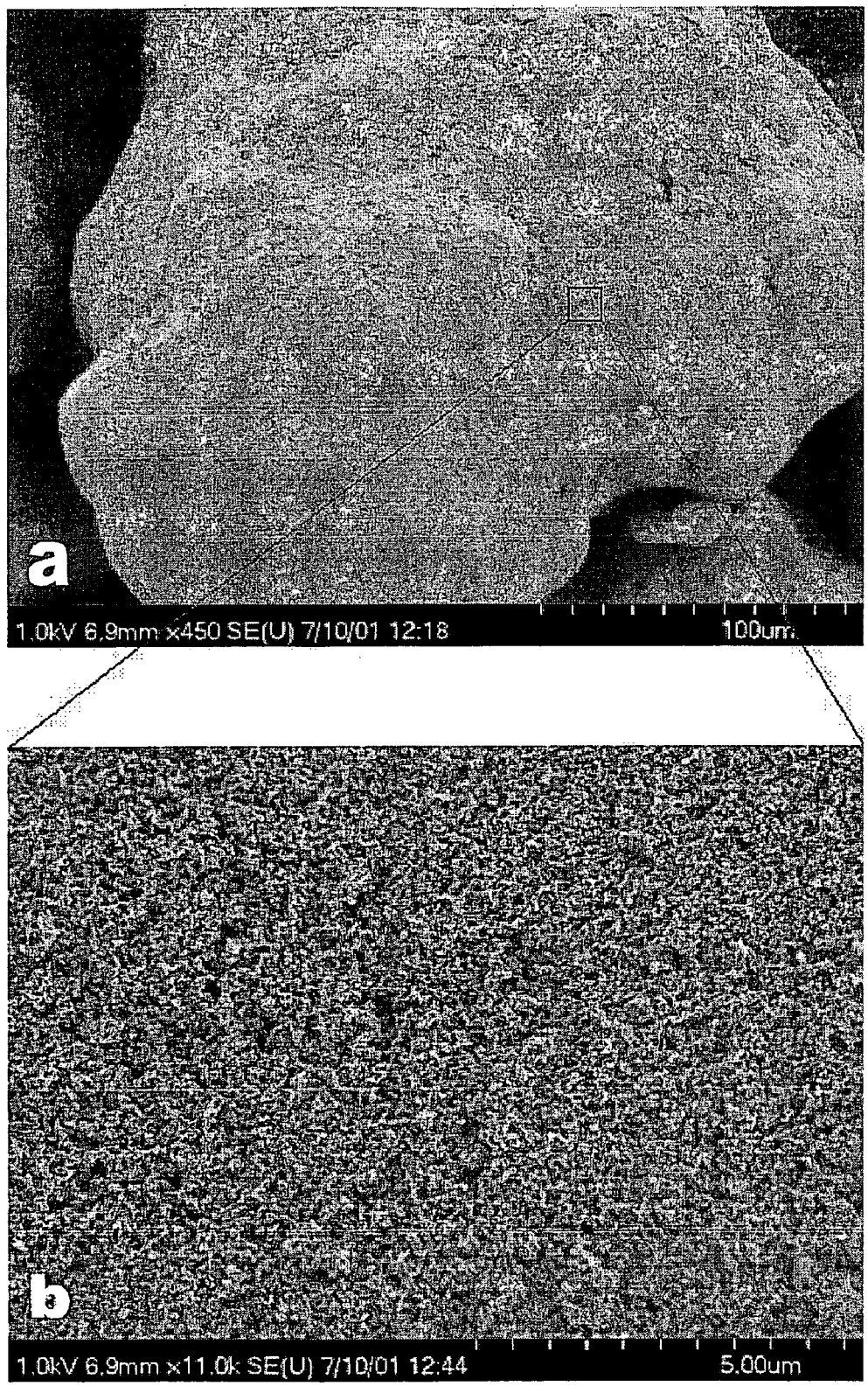
FIG. 6A and 6B are SEM images of a single UHMWPE granule following formation of a powder mixture including 8 wt % carbon black with UHMWPE.

Upon dry mixing the particulate conductive filler with the larger particulate polymer material with suitable energy, the smaller granules of conductive filler material can completely coat the larger polymer granules. For instance, FIG. 6A and 6B show FESEM micrographs of a single powder particle obtained following mixing of 8 wt % carbon black with 92 wt % UHMWPE. As can be seen, the UHMWPE particle is completely coated with carbon black aggregates. While not wishing to be bound by any particular theory, it is believed that forces of mixing combined with electrostatic attractive forces between the non-conductive polymeric particles and the smaller conductive particles are primarily responsible for breaking the agglomerates of the conductive material down into smaller aggregates and forming and holding the coating layer of the conductive material on the polymer particles during formation of the composite powder as well as during later conversion of the powdered composite material into a solid form.

Following formation of the mixture including a conductive filler and a polymeric material, the mixture can be converted as desired to form a solid composite material that is electrically conductive. The solid composite thus formed can also maintain the physical characteristics of the polymer in those embodiments including a relatively low filler level in the composite. For example, in the embodiment described above, in which the composite material includes a conductive filler mixed with UHMWPE, the powder can be converted via a compression molding process or a RAM extrusion process, as is generally known in the art, optionally followed by machining of the solid molded material, for instance in those embodiments wherein a contact sensor describing a complex contact surface curvature is desired.

In other embodiments however, and primarily depending upon the nature of the polymeric portion of the composite, other conversion methods may preferably be employed. For example, in other embodiments, the polymeric portion of the composite material can be a polymer, a co-polymer, or a mixture of polymers that can be suitable for other converting processes, and the composite polymeric material can be converted via, for instance, a relatively simple extrusion or injection molding process.

The composite material of the disclosed sensors can optionally include other materials, in addition to the primary polymeric component and the conductive filler discussed above. Other fillers that can optionally be included in the disclosed composite materials of the present invention can include, for example, various ceramic fillers, aluminum oxide, zirconia, calcium, silicon, fibrous fillers, including carbon fibers and/or glass fibers, or any other fillers as are generally known in the art. In one embodiment, the composite material can include an organic filler, such as may be added to improve sliding properties of the composite material. Such fillers include, for instance, tetrafluoroethylene or a fluororesin.

Figure 7:
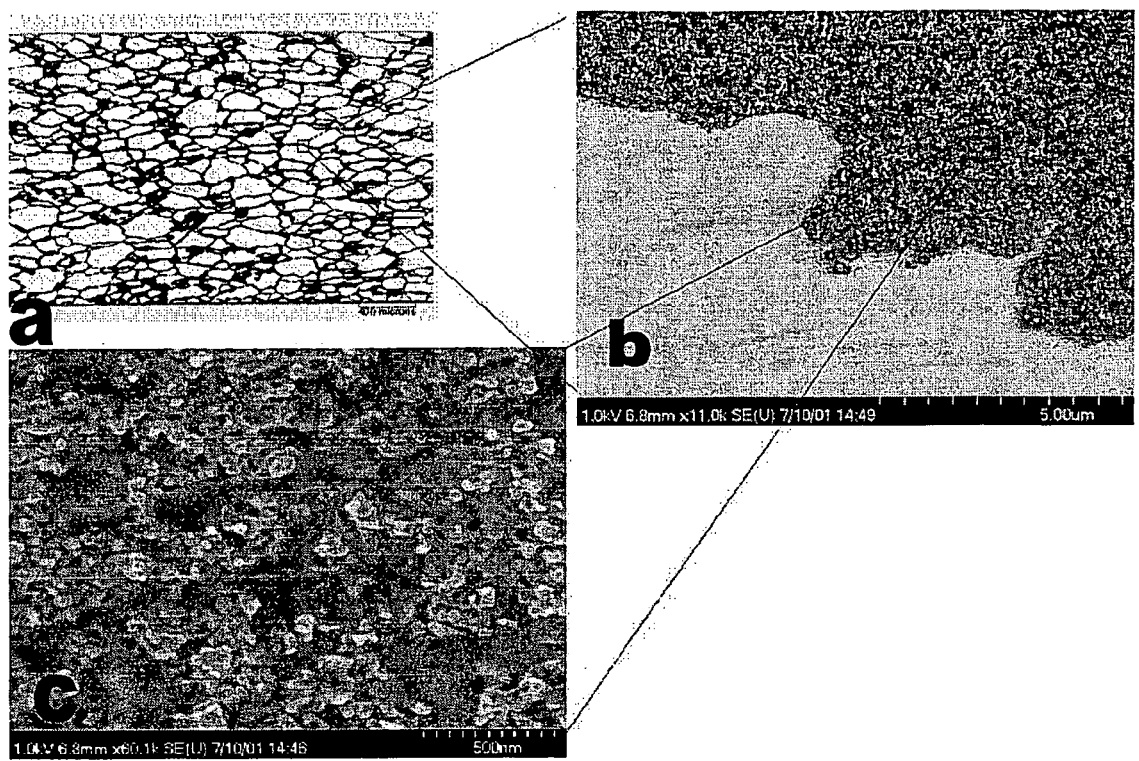
FIGS. 7A-7C are images of increasing magnification of a section of an UHMWPE/CB composite material following compression molding formed according to the present invention.

FIGS. 7A-7C are images of a composite material of the present invention including 8 wt % carbon black and UHMWPE following compression molding of the dry mixture. FIG. 7A is a view obtained by optical microscopy showing a segregated network structure including conductive carbon black-containing channels, with the boxed section magnified in an FESEM image shown in FIG. 7B. As can be seen in FIG. 7B, the junction between the channel region and the non-channel region of the composite material is quite abrupt, showing that the carbon black particles did not flow while the composite material was molded above the melt temperature of the polymer. Thus, it is believed that during the conversion process, the polymer particles can fuse together and confine the conductive filler particles to a three-dimensional channel network within the composite, forming a segregated network type of composite material. FIG. 7C, which is the boxed portion of FIG. 7B at increased magnification, clearly shows individual carbon black primary particles and small aggregates under 200 nm in size (with some under 50 nm in size) well dispersed and embedded in the polymer. As can also be seen in FIG. 7C, the distances between many of the individual carbon black primary particles and small aggregates is quite small, believed to be nearing 10 nm. As is generally known in the art, when two conductive filler particles are within about 10 nm of each other, they can conduct current via electron tunneling, or percolation, with very little resistance. Referring to FIG. 7C, many conductive paths meeting this requirement can be traced across the image. Moreover, as the polymers are deformable, the conductivity, and in particular the resistance, of the composite material of the present invention can vary upon application of a compressive force (i.e., load) to the composite material.

Accordingly, following any desired molding, shaping, cutting and/or machining and also following any desired physical combination of the formed composite material with other non-conductive materials (various embodiments of which are discussed further below), the composite materials of the present invention can be formed into the sensor shape and placed in electrical communication with a data acquisition terminal that can include, for instance, oscilloscopes and/or a computer including suitable recognition and analysis software that can receive and analyze a stream of data from the sensor. For example, in one embodiment, the composite material of the sensor can be hard wired to a data acquisition terminal, such as by machining the composite material to accept a connector of a predetermined geometry within the material itself. A suitable connector can be attached to the composite material with a conductive adhesive, such as a silver ink, for instance. Other connection regimes as are generally known in the art may optionally be utilized, however, including fixed or unfixed connections to any suitable communication system between the composite material and the data acquisition terminal. In particular, no particular electrical communication system is required of the present invention. For instance, in other embodiments, the electrical communication between the composite material and the data acquisition terminal can be wireless, rather than a hard wired connection.

As electrical communications methods and electrical data analysis methods and systems are generally known in the art, these particular aspects of the disclosed contact sensor systems are not described in great detail herein.

In one embodiment, the contact sensor can include only a single sensing point. For example, the entire contact surface of the disclosed sensors can be formed of the conductive composite material. According to this embodiment, the contact sensors can be utilized to obtain impact data and/or the total load on the surface at any time. Such an embodiment can be preferred, for example, in order to obtain total load or impact data for a member without the necessity of having external load cells or strain gauges in communication with the load-bearing member. This sensor type may be particularly beneficial in those embodiments wherein the sensor is intended to be incorporated with or as the member for use in the field. For instance, any polymeric load-bearing member utilized in a process could be formed from the physically equivalent but conductive composite material according to the present invention and incorporated into the working process to provide real time wear and load data of the member with no cost in wear performance to the member due to the acquisition of conductive capability.

In other embodiments, the sensors of the present invention can include multiple sensing points and can provide more detailed data about the junction or the members forming the junction. For instance, multiple sensing points can provide data describing the distribution of contact stresses and/or internal stresses, data concerning types of wear modes, or data concerning a lubrication regime as well as load and impact data for a member forming a junction. According to this embodiment, the composite material can be located at predetermined, discrete regions of a sensor to form multiple sensing points on or in the sensor and a non-conductive material can separate the discrete sensing points from one another. Data from the multiple discrete sensing points can then be correlated and analyzed and can provide information concerning, for instance, the distribution of contact characteristics across the entire mating surface, and in particular can provide contact information under dynamic loading conditions involving, for example, sliding, rolling, or grinding motions across the surface of the sensor.

FIG. 1 is a schematic diagram of one embodiment of the sensor of the present invention including multiple sensing points at the essentially inflexible contact surface of the junction member. Surface sensing points such as those in this embodiment can be utilized to determine contact surface data, including, for example, contact stress data, lubrication data, impact data, and information concerning wear modes. The polymeric sensor 10 includes a contact surface 8 for contact with a metallic component (not shown) to simulate the dynamic characteristics of the joint formed between the sensor and the metallic component. In this particular embodiment, the contact surface 8 describes a curvature to simulate that of the tibial plateau of an artificial knee implant.

As can be seen with reference to FIG. 1, the sensor 10 includes multiple sensing points 12 at the contact surface 8 of the sensor 10. The sensing points 12 can be formed of the conductive composite material as herein described. Upon contact of a single sensing point 12 with the metallic component, an electrical signal can be generated and sent via wire 18 to a data acquisition location. Though not expressly shown in the Figure, in this particular embodiment, every single sensing point 12, can be wired so as to provide data from that point to the data acquisition location. Due to the deformable nature of the polymeric composite material, the characteristics of the generated electrical signal can vary with the variation in load applied at the sensing point 12 and a dynamic contact stress distribution profile for the joint can be developed.

The surface area and geometry of any individual sensing point 12 as well as the overall geometric arrangement of the plurality of sensing points 12 over the surface 8 of the sensor 10, can be predetermined as desired. For example, through the formation and distribution of smaller sensing points 12 with less intervening space between individual sensing points 12, the spatial resolution of the data can be improved. While there may be a theoretical physical limit to the minimum size of a single sensing point determined by the size of a single polymer granule, practically speaking, the minimum size of the individual sensing points will only be limited by modern machining and electrical connection forming techniques. In addition, increased numbers of data points can complicate the correlation and analysis of the data. As such, the preferred geometry and size of the multiple sensing points can generally involve a compromise between the spatial resolution obtained and complication of formation methods.

In this particular embodiment as seen in FIG. 1, the composite material forming the surface sensing points 12 can extend to the base 15 of the sensor 10, where electrical communication can be established to a data acquisition and analysis location (not shown), such as a computer with suitable software, for example.

The discrete sensing points 12 of the sensor 10 of FIG. 1 are separated by a non-conductive material 14 that can, in one embodiment, be formed of the same polymeric material as that contained in the composite material forming the sensing points 12. In general, the method of combining the two materials to form the sensor can be any suitable formation method. For example, in one embodiment the composite material can be formed into the desirable shape, such as multiple individual rods of composite material as shown in the embodiment illustrated in FIG. 1, and then these discrete sections can be inserted into a block of the non-conductive polymer that has had properly sized holes cut out of the block. Optionally, the two polymeric components of the sensor can then be fused, such as with heat and/or pressure, and any final shaping of the two-component sensor, such as surface shaping via machining, for instance, can be carried out so as to form the sensor 10 including discrete sensing points 12 formed of the conductive composite material at the surface 8.

While not a requirement of the invention, it may be preferable in many embodiments of the invention to utilize the same material but for the presence or absence of the conductive filler for the composite sensing points 12 as for the intervening spaces 14 since, as described above, the physical characteristics of the composite material can be essentially identical to the physical characteristics of the non-conductive material used in forming the composite. According to this embodiment, the sensor 10 can have uniform physical characteristics across the entire sensor 10, i.e., both at the sensing points 12 and in the intervening space 14 between the composite material.

In one particular embodiment, the polymer used to form the sensor 10 can be the same polymer as is used to form the member for use in the field. For example, when considering the examination of artificial joints, the polymer used to form both the composite material at the sensing points 12 and the material in the intervening space 14 between the sensing points 12 can be formed of the same polymer as that expected to be used to form the polymeric bearing component of the implantable device (e.g., UHMWPE or polyurethane). Thus, the sensor 10 can provide real time, accurate, dynamic contact data for the implantable polymeric bearing under expected conditions of use.

Optionally, the surface 8 of the sensor 10 can be coated with a lubricating fluid, and in particular, a lubricating fluid such as may be utilized for the bearing during actual use and under the expected conditions of use (e.g., pressure, temperature, etc.). In this embodiment, in addition to providing direct contact data, the disclosed sensors can also be utilized to examine data concerning contact through an intervening material, i.e., lubrication regimes under expected conditions of use. For instance, the sensor can be utilized to determine the type and/or quality of lubrication occurring over the surface of the sensor including variation in fluid film thickness across the surface during use. In one embodiment, this can merely be determined by presence or absence of fluid, e.g., presence or absence of direct contact data (i.e., current flow) in those embodiments wherein the fluid is a non-conductive lubricating fluid. In other embodiments, a more detailed analysis can be obtained, such as determination of variation in fluid film thickness. This information can be obtained, for example, by comparing non-lubricated contact data with the data obtained from the same joint under the same loading conditions but including the intervening lubricant. In another embodiment, such information could be obtained through analysis of the signal obtained upon variation of the frequency and amplitude of the applied voltage. In yet another embodiment, the sensor can be utilized in a capacitance mode, in order to obtain the exact distance between the two surfaces forming the joint. In one particular embodiment, the disclosed sensor can be utilized to determine a lubrication distribution profile of the contact surface over time.

Figure 2:
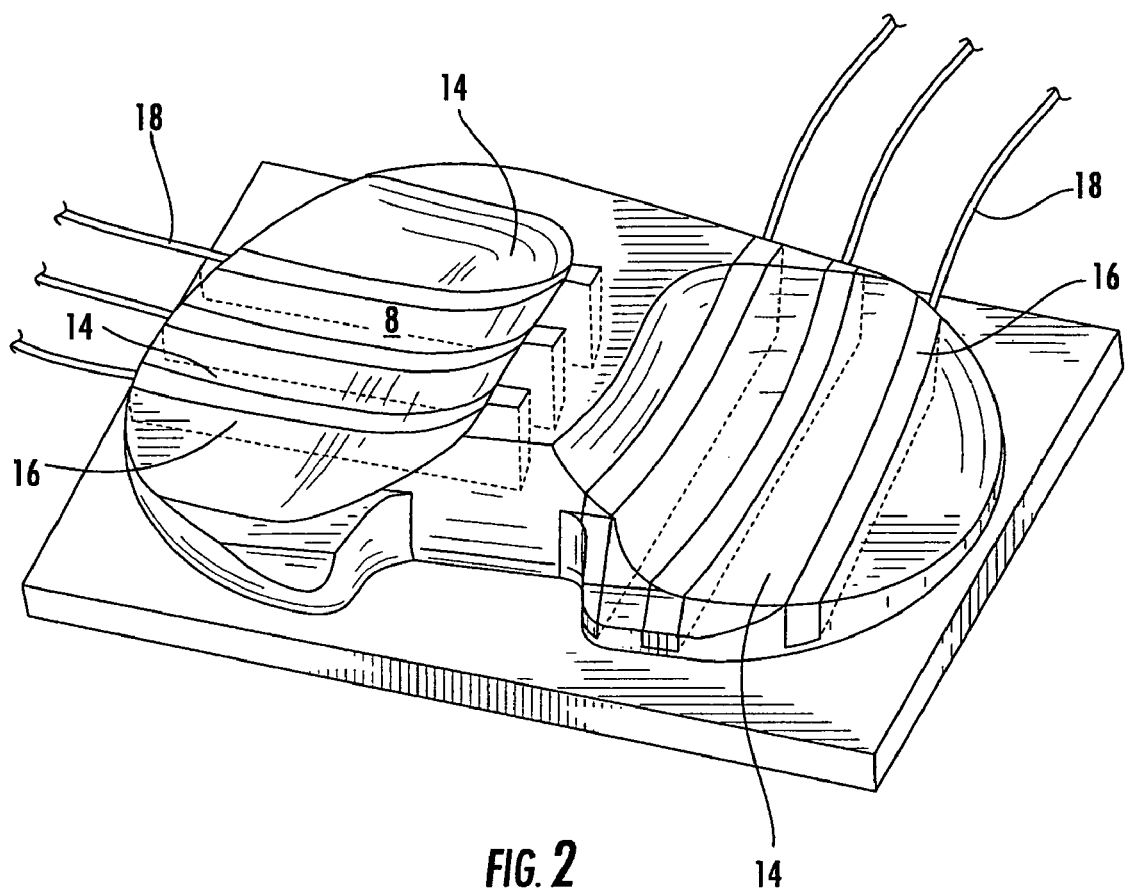
FIG. 2 illustrates another embodiment of the present invention for obtaining surface contact data of a junction.

FIG. 2 illustrates another embodiment of the contact sensors of the present invention. According to this embodiment, the sensor includes multiple sensing strips 16 across the surface 8 of the sensor 10. As illustrated, in this embodiment, the orientation of the individual sensing strips 16 across the different condoyles formed on the single sensor surface can be varied from one another. Alternatively, strips can be laid in different orientations on separate but identically shaped sensors in a multi-sensor testing apparatus. In any case, by varying the orientation of sensor strips on multiple, but essentially identical surfaces, virtual cross-points can be created when the data from the different surfaces is correlated. In particular, when contacts of the same shape and magnitude at the same location of different surfaces is recognized, a virtual data point at the cross-point can be created. As can be seen in the Figure, this embodiment can necessitate the formation of fewer electrical connections and wires 18 in order to provide data to the acquisition and analysis location, which may be preferred in some embodiments due to increased system simplicity.

Figure 3:
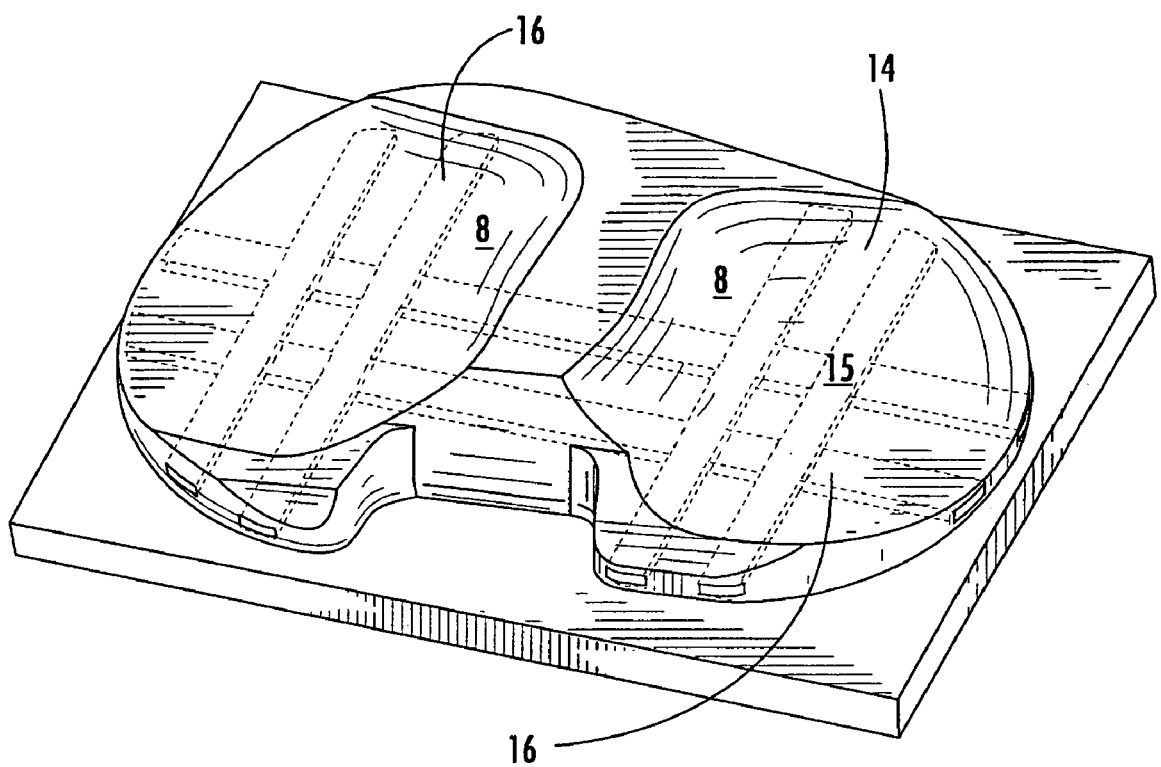
FIG. 3 illustrates another embodiment of the present invention for obtaining sub-surface contact data of a junction.

Optionally, the contact sensors of the present invention can be utilized to provide sub-surface stress data. For example, in the embodiment illustrated in FIG. 3, multiple sensing strips 16 can be located within a subsurface layer at a predetermined depth of the sensor. According to this embodiment, the horizontal and vertical strips 16 can cross each other with a conductive material located between the cross points to form a subsurface sensing point 15 at each cross point. In one embodiment, the strips 16 can be formed of the composite material described herein with the intervening material being the same basic composite material but with a lower weight percentage of the conductive filler, and the layer can be laid within the insulating non-conductive polymer material 14. In another embodiment, the sensing strips 16 can be any conductive material, such as a metallic wire, for example, laid on either side of a sheet or section of the composite material, and the layer can then be located at a depth from the surface 8 of the sensor.

Application of a load at the surface 8 of the sensor can then vary the electronic characteristics at the internal sensing point 15. In particular, the current flow at any point 15 can vary in proportion to the stress at that point. Thus, when data from multiple sensing points 15 are correlated, an internal stress profile for the sensor can be developed at that particular depth.

In another embodiment, the sensors can include multiple layers at different depths from the surface 8, each layer including one or more internal stress points 15. According to this particular embodiment, a stress profile as a function of depth from the surface 8 can be developed for the sensor.

In yet another embodiment, both subsurface contact data and surface contact data can be gathered from a single sensor through combination of the above-described embodiments.

The present invention may be better understood with reference to the Examples, below.

EXAMPLE 1

An industrial-grade UHMWPE powder (GUR 1150, available from Ticona Engineering Polymers) having a molecular weight of $6 \times 10^6$, density of 0.93 g/mL, $T_m$ of 135° C., and an average particle size of 100 μm, was combined with carbon black (CB) (Printex L-6 available from Degussa Hulls, Dusseldorf, Germany) having a primary particle size of 18 nm and dibutyl phthalate absorption of 120 mL/100 g. Amounts of each powder were placed in a 120 mL plastic sample container and initially manually shaken for 5 minutes to obtain four different samples having CB weight percentages of 0.25%, 0.5%, 1%, and 8%. The samples were then mixed for 10 minutes on a common laboratory vortex at the maximum speed setting.

Virgin UHMWPE powder and the four UHMWPE/CB powder mixtures were then compression-molded into rectangular sheets 12 cm long, 8.5 cm wide, and 2 mm thick using a mold consisting of a 2 mm thick Teflon frame sandwiched between 2 stainless steel plates that were coated with Teflon mold release spray. The powders were processed in a laboratory press (Carver Laboratory Press, Model C, Fred S. Carver Inc., Wabash, Ind.) equipped with electric heaters for 20 minutes at a temperature of 205° C. and a pressure of 10 MPa. The specimens were then quenched under pressure at a cooling rate of 50 ° C./min.

FIG. 7A-7C, discussed in more detail above, are images of the composite material including 8 wt % CB following compression molding of the powder.

Figure 8:
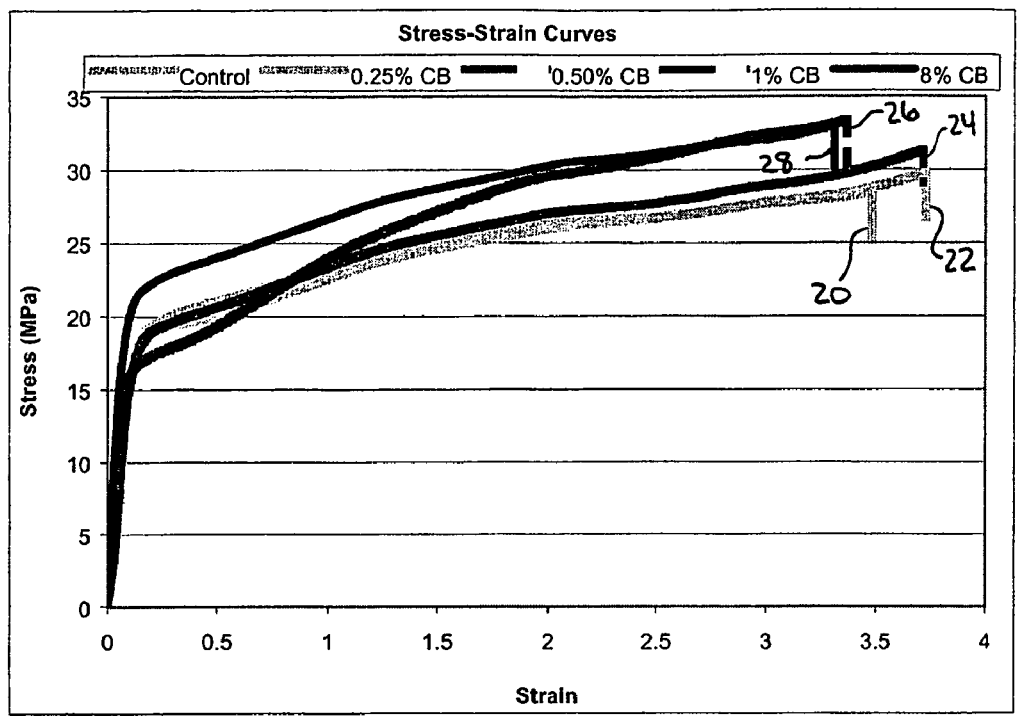
FIG. 8 graphically illustrates the stress v. strain curve for exemplary composite conductive materials of the present invention.

Tensile tests were performed to obtain stress-strain curves for each composite and for the control. Results can be seen in FIG. 8 for the control (20), 0.25% CB (22), 0.50% CB (24), 1.0% CB (26), and 8.0% CB (28). From these stress-strain curves, the modulus of elasticity was determined for each composite, and these values were compared to those obtained for the control specimen. Both the control specimens and the composite specimens were formed from the same stock of virgin UHMWPE powder (GUR 1150) by using the same processing parameters of temperature, pressure, time, and cooling rate. The results from the tensile tests can be seen in Table 3, below. It was determined that there was no statistically significant difference (p=0.32, $\alpha$=0.05) between the modulus of the 8% composite and the modulus of the virgin UHMWPE control samples that were tested.

| n = 4 | Control | 0.25 wt % CB | 0.50 wt % CB | 1 wt % CB | 8 wt % CB |
|---|---|---|---|---|---|
| Young's Modulus (MPa) | 214.8 ± 21.1 | 208.48 ± 7.68 | 211.9 ± 7.74 | 212.6 ± 6.82 | 208.9 ± 11.1 |
| Tensile Strength (MPa) | 30.8 ± 3.98 | 29.1 ± 2.23 | 32.6 ± 3.49 | 31.9 ± 2.43 | 31.7 ± 1.03 |
| Yield Strength (MPa) | 17.8 ± 0.75 | 18.0 ± 0.87 | 17.8 ± 0.93 | 15.2 ± 0.96 | 22.2 ± 1.07 |
| Elongation at Break (%) | 390 ± 77.0 | 360 ± 18.0 | 390 ± 18.0 | 340 ± 23 | 290 ± 41 |

The elastic modulus values obtained were comparable to those obtained by Parasnis and colleagues for thin-film UHMWPE specimens (see Parasnis C, Ramani K. Analysis of the effect of pressure on compression molding of UHMWPE. Journal of Materials Science: Materials in Medicine, Vol. 9, p 165-172, 1998, which is incorporated herein by reference). The values obtained for tensile strength, yield strength, and elongation at break compared closely to the values cited in the literature (for example, see is Li S. Burstein A.H., Current Concepts Review: Ultra-high molecular weight polyethylene. The Journal of Bone and Joint Surgery, Vol. 76-A, No. 7, p 1080-1090, 1994, which is incorporated herein by reference).

Figure 9:
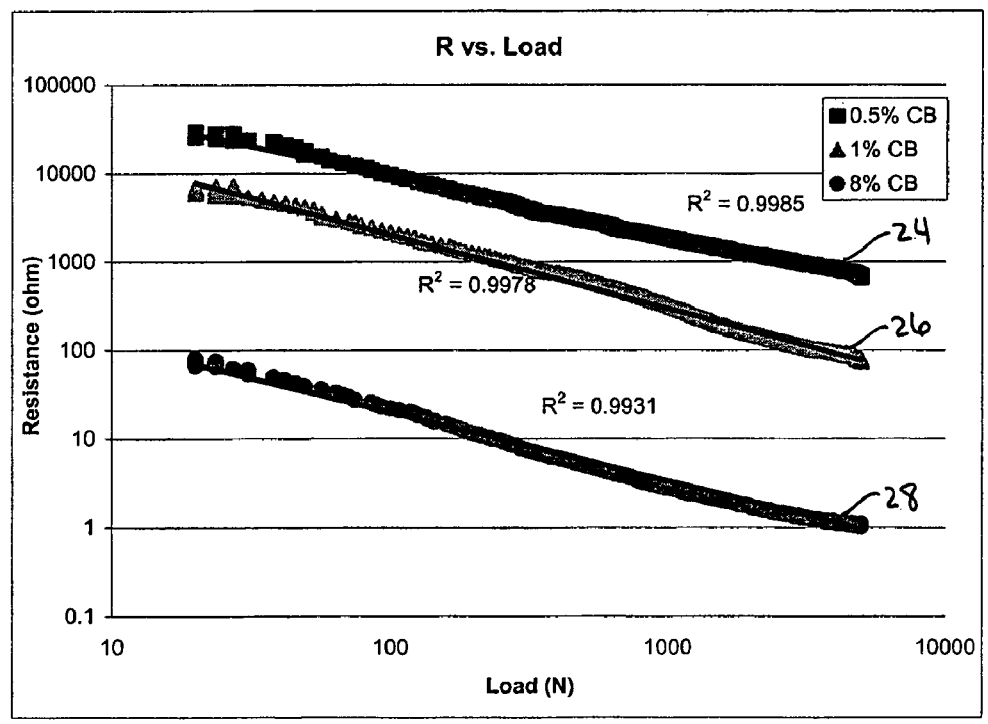
FIG. 9 graphically illustrates the log of resistance vs. log of the load for three different composite conductive materials of the present invention.
Figure 10:
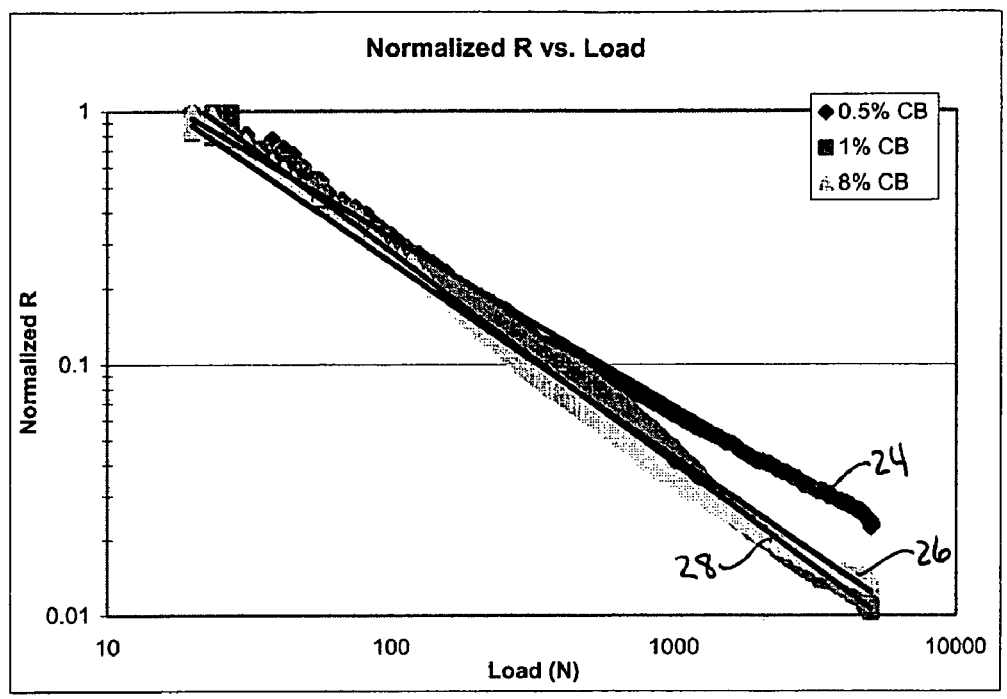
FIG. 10 illustrates the log of normalized resistance vs. log of the load for three different composite conductive materials of the present invention.

FIG. 9 shows a plot of the log of the resistance as a function of the log of the compressive load applied to the UHMWPE/CB composites of 0.5% (24), 1% (26), and 8% (28). The plot shows that the composites have the same slope, but that the intercepts are different, with the 0.5% composite having the highest intercept, and the 8% composite having the lowest intercept. The value of resistance changed by about two orders of magnitude for each composite. The correlation coefficients of each regression line indicated a good fit. When the values of resistance were normalized (shown in FIG. 10), the curves for the three composites were very similar, suggesting that the amount of CB only affected the magnitude of the resistance. Thus, the relative response to applied load appeared to be independent of the amount of CB. It should be noted that the control sample and the 0.25% CB sample had high resistance for all loads tested and thus were not included on FIGS. 9 and 10.

Figure 11:
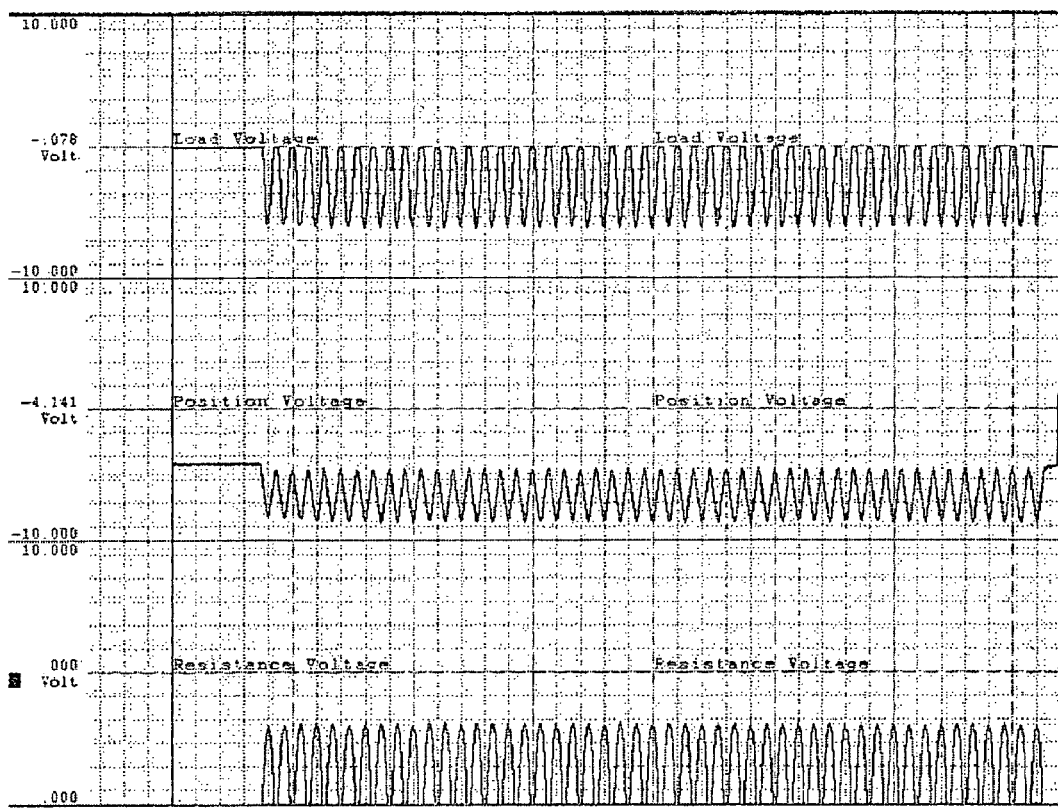
FIG. 11 illustrates the voltage values corresponding to load, position, and resistance of an exemplary composite material.

FIG. 11 shows the voltage values corresponding to the compressive load, the compressive displacement, and the resistance of the 8 wt % CB composite while the composite was loaded cyclically with a haversine wave at 1 Hz. The top curve corresponds to the compressive stress, the middle curve corresponds to the compressive strain, and the bottom curve corresponds to the resistance of the sensor material. This data represents the cyclic response of the material, indicating that it does not experience stress-relaxation at a loading frequency of 1 Hz. The results of this cyclic testing show that the peak voltage values corresponding to resistance remain nearly constant over many cycles. Therefore, the data seem to indicate that the sensor material should be well suited for cyclic measurements since the readings do not degrade over time.

Monitoring the electrical resistance of the composite material while applying a compressive load revealed the force-dependent nature of the electrical properties of the material. Because of the nano-scale dispersion of the conductive filler, the material's electrical response to applied load was nearly ideal for all of the percentages tested. That is, the log of the material's resistance varied linearly with respect to the log of the applied load. This linear relationship makes the material well suited for use as a sensor.

The data show that the linear relationship holds true for 0.5%, 1%, and 8%, with the difference between the three being the value of the resistance. As all three percentages showed good sensor properties, specific formulations could be developed based on other criteria, such as the specifics of the measurement electronics.

EXAMPLE 2

Compression molding was used to form 2 rectangular blocks of 1150 UHMWPE doped with 8 wt % carbon black filler as described above for Example 1. The blocks formed included a 28×18 matrix of surface sensing points 12 as shown in FIG. 1. The points were circular with a $\frac{1}{16}^{th}$ inch (1.59 mm) diameter and spaced every $\frac{1}{10}^{th}$ inch (2.54 mm). The blocks were then machined to form both a highly-conforming, PCL-sacrificing tibial insert (Natural Knee II, Ultra-congruent size 3, Centerpulse Orthopedics, Austin, Tex.) and a less conforming PCL-retaining tibial insert (Natural Knee II, Standard-congruent, size 3, Centerpulse Orthopedics, Austin, Tex.) as illustrated in FIG. 1. The implants were then aligned and potted directly in PMMA in the tibial fixture of a multi-axis, force-controlled knee joint simulator (Stanmore/Instron, Model KC Knee Simulator). Static testing was performed with an axial load of 2.9 kN (4×B.W.) at flexion angles of 0°, 30°, 60°, and 80°, to eliminate the effects of lubricant and to compare the sensor reading to the literature. The dynamic contact area was then measured during a standard walking cycle using the proposed 1999 ISO force-control testing standard, #14243. Data was collected and averaged over 8 cycles. A pure hydrocarbon, light olive oil was used as the lubricant due to its inert electrical properties.

Static loading of the sensors showed that the contact area of the ultra congruent insert was significantly higher than that of the standard congruent insert at all angles of flexion tested. The data closely agreed with results found in the literature from FEA analysis.

Figure 12:
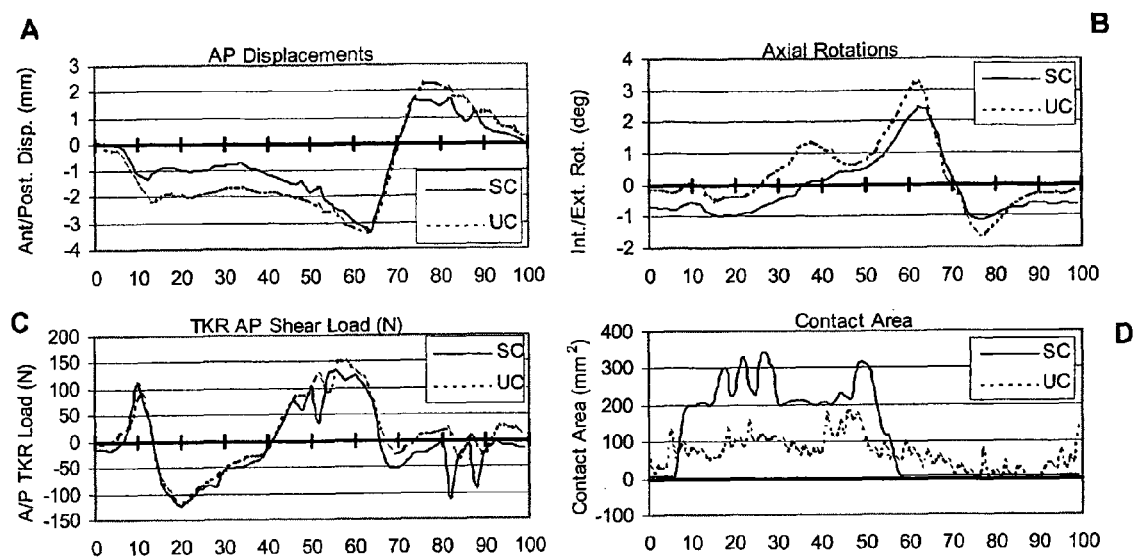
FIGS. 12A-12D illustrate the kinematics and contact area for exemplary artificial knee implant sensors of the present invention with different surface geometries.

The results from dynamic testing with a standard walking protocol, shown in FIG. 12, show the effects that the lubricant had on the dynamic contact area. Contact area was registered by the sensor when physical contact occurred between the femoral component and any sensing point, allowing electrical current to flow. Because the lubricant was electrically insulating, fluid-film lubrication over a sensing point caused no contact to be registered at that point. The lower contact area measured for the ultra-congruent insert during the stance phase of gait was due to the fluid-film lubrication that occurred with the more conforming insert. The rapid changes in contact area measured for the standard-congruent insert during the mid-stance phase suggests that the mode of lubrication is quite sensitive to the dynamic loading patterns.

EXAMPLE 3

Figure 13A:
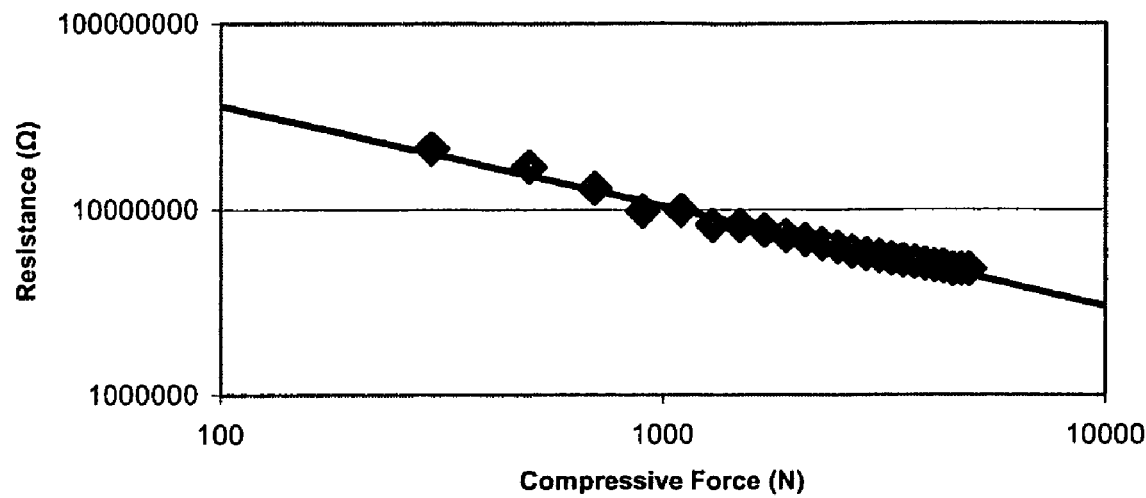
FIGS. 13A and 13B graphically illustrate the log of normalized resistance vs. log of the compressive force for two different composite conductive materials of the present invention.
Figure 13B:
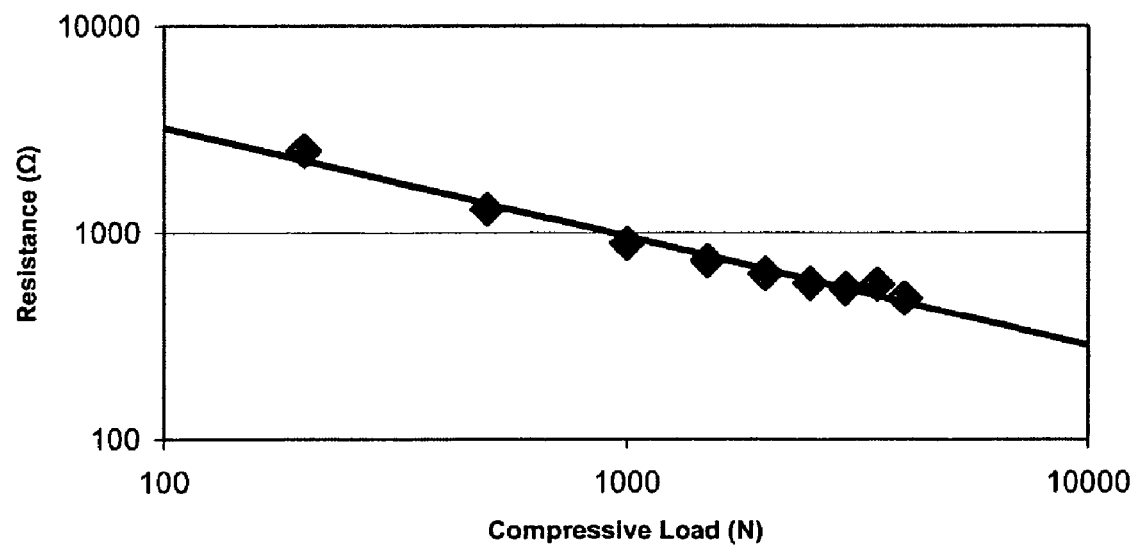

Tecoflex SG-80A, a medical grade soft polyurethane available from Thermedics Inc. (Woburn, Mass.), was solution processed and molded including 4 wt % and 48 wt % CB to form two solid sample materials. FIGS. 13A and 13B graphically illustrate the resistance vs. compressive force applied to the samples for the 4% and 48% non-surfactant mixed samples, respectively. As can be seen, both samples showed pressure sensitive conductive characteristics suitable for forming the sensors of the present invention where the value of resistance can be controlled with the amount of conductive filler added.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A contact sensor comprising:
an essentially inflexible electrically conductive composite material at a surface, the electrically conductive composite material comprising an essentially inflexible high performance or engineering polymer and an essentially inflexible conductive filler;
a conductive member; and
a junction being defined between the electrically conductive composite material at the surface and the conductive member;
wherein variations in load between the electrically conductive composite material and the conductive member produce an output signal representative of the detectable variations in resistance at the surface of the electrically conductive composite material due to contact between the surface of the electrically conductive composite material and the conductive member.

2. The contact sensor of claim 1, wherein the conductive composite material comprises less than about 10% by weight of the conductive filler.

3. The contact sensor of claim 1, wherein surface defines curvature.

4. The contact sensor of claim 1, wherein the surface comprises discrete regions of the electrically conductive composite material separated by an intervening material.

5. The contact sensor of claim 4, wherein the intervening material comprises the same polymer as the polymer of the electrically conductive composite material.

6. The contact sensor of claim 1, wherein the polymer is an ultra-high molecular weight polyethylene or polyurethane.

7. The contact sensor of claim 1, wherein the conductive filler comprises carbon black.

8. The contact sensor of claim 1, wherein the contact sensor is in electrical communication with a data acquisition terminal.

9. The contact sensor of claim 1, wherein the conductive composite material comprises less than about 8% by weight of the conductive filler.

10. The contact sensor of claim 1, wherein the conductive composite material comprises less than about 5% by weight of the conductive filler.

11. A method of forming the contact sensor of claim 1, the method comprising:

mixing the polymer in particulate form with the conductive filler in particulate form to form the composite conductive material, wherein the composite conductive material comprises less than about 10% by weight of the conductive filler, wherein the average particle size of the polymer is at least about two orders of magnitude larger than the average particle size of the conductive filler.

12. The method of claim 11, wherein the average particle size of the polymer is between about 50 μm and about 500 μm.

13. The method of claim 11, wherein the average particle size of the conductive filler is between about 10 nm and about 500 nm.

14. The method of claim 11, further comprising molding the mixed polymer and conductive filler according to a molding process selected from the group consisting of compression molding, RAM extrusion, screw extrusion, and injection molding.

15. The method of claim 11, wherein the surface of the contact sensor is formed so as to define a curvature.

16. The method of claim 11, further comprising establishing electrical communication between the contact sensor and a data acquisition terminal for examining the output signal from the contact sensor.

17. A method for determining contact data at a junction comprising:

providing the contact sensor of claim 1, the contact sensor being in electrical communication with a data acquisition terminal; and gathering contact data at the data acquisition terminal.

18. The method of claim 17, wherein the data comprises dynamic contact data.

19. The method of claim 17, wherein the surface defines a shape concordant with the contact surface of a polymeric bearing of a biocompatible implantable artificial replacement joint.

20. The method of claim 17, further comprising lubricating the junction.

21. The method of claim 20, wherein the data comprises lubrication regime data.

22. The method of claim 17, wherein the contact sensor gathers data concerning contact between the essentially inflexible electrically conductive composite material and the conductive member in real time in an industrial setting.

23. The method of claim 17, wherein the contact data comprises at least one output signal.

\* \* \* \* \*